(12) United States Patent  
Dietze et al.

(10) Patent No.: US 11,114,574 B2  
(45) Date of Patent: Sep. 7, 2021

(54) SEMICONDUCTOR SENSOR

(71) Applicant: OSRAM Opto Semiconductors GmbH, Regensburg (DE)

(72) Inventors: Daniel Dietze, Regensburg (DE); Tim Boescke, Regensburg (DE); Wolfgang Zinkl, Tegernheim (DE)

(73) Assignee: OSRAM Opto Semiconductors GmbH, Regensburg (DE)

( * ) Notice: Subject to any disclaimer, the term of this patent is extended or adjusted under 35 U.S.C. 154(b) by 117 days.

(21) Appl. No.: 16/624,969

(22) PCT Filed: Jun. 13, 2018

(86) PCT No.: PCT/EP2018/065695  
§ 371 (c)(1),  
(2) Date: Dec. 20, 2019

(87) PCT Pub. No.: WO2018/234123  
PCT Pub. Date: Dec. 27, 2018

(65) Prior Publication Data  
US 2020/0176616 A1    Jun. 4, 2020

(30) Foreign Application Priority Data  
Jun. 20, 2017 (DE) .................... 10 2017 113 535.9

(51) Int. Cl.  
*H01L 31/0216* (2014.01)  
*A61B 5/024* (2006.01)  
(Continued)

(52) U.S. Cl.  
CPC .... *H01L 31/02165* (2013.01); *A61B 5/02433* (2013.01); *H01L 27/1446* (2013.01);  
(Continued)

(58) Field of Classification Search  
CPC ............ H01L 27/1446; H01L 27/1462; H01L 27/14621; H01L 31/02165;  
(Continued)

(56) References Cited

U.S. PATENT DOCUMENTS 4,865,405 A    9/1989   Kageyama  
8,809,099 B2   8/2014   Wang et al.  
(Continued)

FOREIGN PATENT DOCUMENTS

DE    30 48 879 A1    9/1981  
DE    203 15 422 U1   12/2003  
(Continued)

*Primary Examiner* — Ermias T Woldegeorgis  
(74) *Attorney, Agent, or Firm* — DLA Piper LLP (US)

(57) ABSTRACT

A semiconductor sensor includes a detector chip that detects green light and an interference filter that optically precedes the detector chip and is permeable to green light and impermeable and reflective to red light and near-infrared radiation. A color filter optically precedes the interference filter. The color filter has a transparency of at least 60% for green light and has an absorbing effect for red light and near-infrared radiation. The semiconductor sensor appears gray or black in the region of the interference filter independently of the angle.

15 Claims, 5 Drawing Sheets

(51) Int. Cl.
  *H01L 27/146* (2006.01)
  *H01L 27/144* (2006.01)
  *G02B 5/22* (2006.01)
  *G02B 5/28* (2006.01)

(52) U.S. Cl.
  CPC .... *H01L 27/1462* (2013.01); *H01L 27/14621* (2013.01); *H01L 31/02162* (2013.01); *G02B 5/223* (2013.01); *G02B 5/282* (2013.01)

(58) Field of Classification Search
  CPC .......... H01L 31/02162; A61B 5/02433; G02B 5/223; G02B 5/282
  See application file for complete search history.

(56) References Cited

U.S. PATENT DOCUMENTS

| | | |
|---|---|---|
| 2011/0068255 A1 | 3/2011 | Zheng et al. |
| 2012/0145901 A1 | 6/2012 | Kakiuchi et al. |
| 2012/0187515 A1* | 7/2012 | Kerness ................ G01J 1/0418 257/432 |
| 2015/0200220 A1 | 7/2015 | Juenger et al. |
| 2016/0118509 A1 | 4/2016 | Altmejd et al. |

FOREIGN PATENT DOCUMENTS

| | | |
|---|---|---|
| DE | 10 2015 117 940 A1 | 4/2017 |
| EP | 1 667 231 A1 | 6/2006 |

* cited by examiner

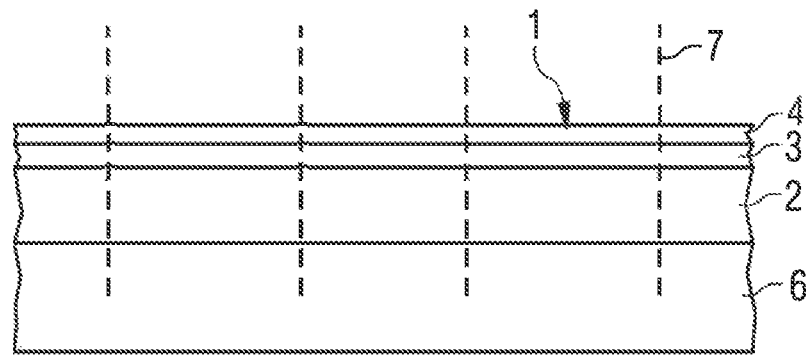
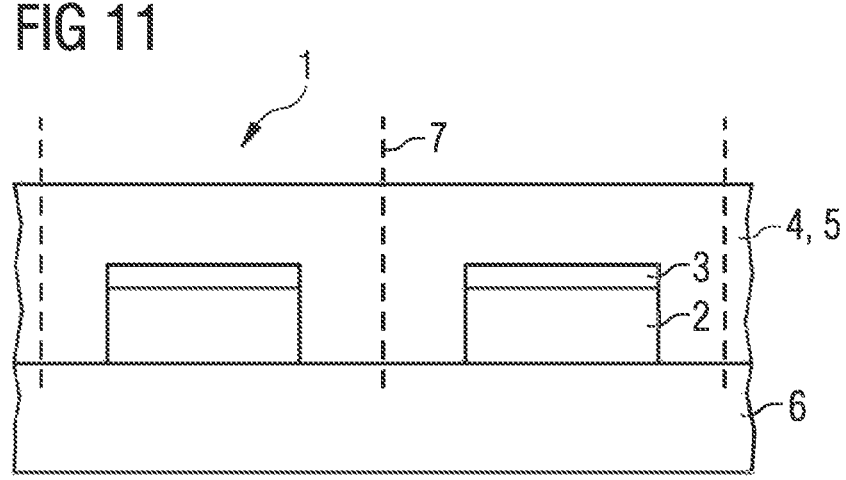
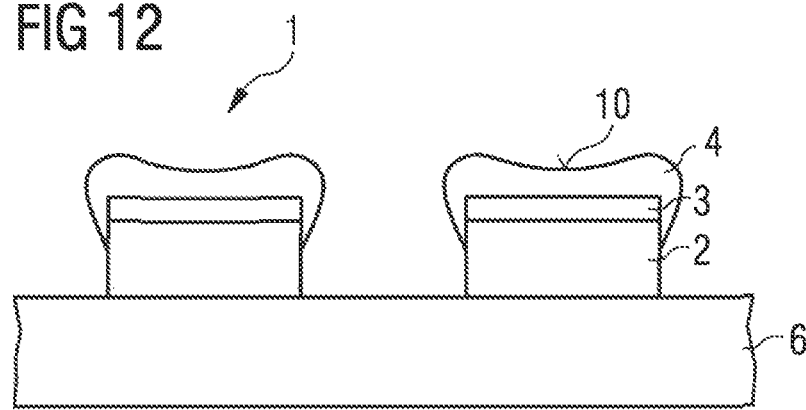

SEMICONDUCTOR SENSOR

TECHNICAL FIELD

This disclosure relates to a semiconductor sensor.

BACKGROUND

U.S. Pat. No. 4,865,405 A discloses an optical filter.

U.S. Pat. No. 8,809,099 B2 discloses a light sensor with an infrared interference filter and a color filter integrated on a semiconductor chip.

An infrared transmission filter and a component therewith is disclosed in US 2012/0145901 A1.

SUMMARY

We provide a semiconductor sensor including a detector chip that detects radiation of a first wavelength range or green light, an interference filter that optically precedes the detector chip and is permeable to the radiation of the first wavelength range or the green light, and impermeable and reflective to radiation of a second wavelength range or red or near-infrared light, a color filter that optically precedes the interference filter, wherein the color filter has a transparency of at least 60% for the first wavelength range or green light, and absorbs radiation of the second wavelength range or red or near-infrared light, and the semiconductor sensor appears gray or black to an observer in a region of the interference filter independently of the angle, the interference filter includes at least one refractive index matching layer that delimits the interference filter toward the color filter, and a cast body in which the interference filter and the detector chip are embedded, wherein the cast body contains least one plastic to which at least one filter material is added, and the cast body extends across the interference filter so that the color filter is formed by the part of the cast body extending across the interference filter.

BRIEF DESCRIPTION OF THE DRAWINGS

FIGS. 10 to 12 are schematic sectional views of method steps of manufacturing semiconductor sensors described herein.

LIST OF REFERENCE SYMBOLS

Figure 1:
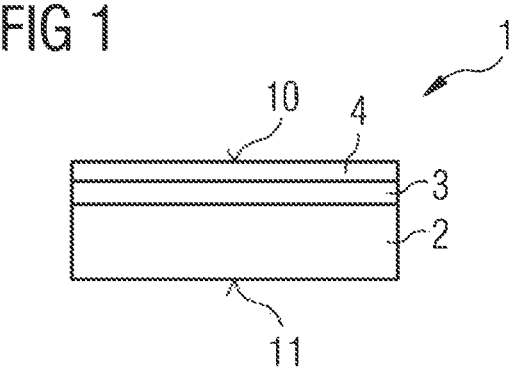
FIGS. 1 to 3 are schematic sectional views of examples of semiconductor sensors described herein.

1 Semiconductor sensor
10 Detection side
11 Mounting side
2 Detector chip
3 Interference filter
31 First layer stack
32 Second layer stack
33 Refractive index matching layer
4 Color filter
5 Cast body
6 Carrier
7 Separation line
D Position along a growth direction in μm
L Wavelength in nm or μm
n Refractive index
R Reflectivity
S Relative spectral sensitivity with filter in %
S' Relative spectral sensitivity without filter in %
T Transmission
VL Eye sensitivity curve

DETAILED DESCRIPTION

Our semiconductor sensor comprises at least one detector chip. The detector chip(s) are configured to detect radiation of a first wavelength range. The detector chip preferably detects green light. In particular, the detector chip is configured to detect light in the wavelength range of 520 nm to 570 nm. That is to say, the first wavelength range may be 520 nm to 570 nm. A plurality of different detector chips can be integrated in the semiconductor sensor, which detector chips are configured to detect radiation of different wavelengths, for example, detect red light and/or near-infrared radiation. However, the semiconductor sensor preferably comprises precisely one detector chip configured to detect green light.

The detector chip may be a sensor such as a photodiode, integrated in a semiconductor chip such as an IC, for example, in CMOS technology in a silicon chip. Thus, the detector chip need not be a discrete photodiode. Rather, the detector chip can be a part of a multifunctional semiconductor chip that additionally comprises, for example, control circuits, memory units and/or communication interfaces.

The semiconductor sensor may comprise an interference filter. The interference filter optically precedes the detector chip. That is to say, light can pass to the detector chip only through the interference filter.

The interference filter may be permeable to radiation of the first wavelength range, i.e., in particular to green light. This means, for example, that a transmission in the spectral range of 520 nm to 570 nm is sporadically or preferably continuously at least 80% or 90% or 95%. In other words, green light preferably passes almost completely through the interference filter.

The interference filter may be impermeable to radiation of a second wavelength range, in particular to red and near-infrared light. In particular, the interference filter is reflective to red and near-infrared light, at least in specific incident angle ranges, especially for perpendicularly incident radiation. This means, for example, that a transmission of light and radiation in the wavelength range, in particular 0.7 μm to 1.1 μm, is at most 10% or 3% or 1%. Accordingly, reflectivity to radiation in this wavelength range is preferably at least 90% or 97% or 99%. That is to say, the interference filter is practically impervious to red and near-infrared light in the wavelength range. Red light denotes in particular wavelengths of 610 nm to 0.7 μm, and near-infrared light denotes wavelengths of 0.7 μm to 1.1 μm. That is to say, the second wavelength range is, in particular, 610 nm to 1.1 μm. Thereby, the lower limit may be replaced by a cutoff wavelength of the interference filter.

The semiconductor sensor may comprise a color filter. A filtering effect of the color filter results in particular from the absorption capacity of components of the color filter. For this purpose, the color filter can have dyes and/or pigments.

The color filter may optically precede the interference filter. This means, in particular, that radiation can only pass through the color filter to the interference filter and preferably also to the detector chip.

The color filter for radiation of the first wavelength range, i.e., especially for green light, may have a transparency, i.e., a transmittance, of at least 60% or 80% or 90%. This means that the color filter preferably allows green light to pass almost without hindrance.

The color filter may absorb radiation of the second wavelength range, i.e., in particular red and/or near-infrared light. The absorption capacity of the color filter in the wavelength of 0.7 μm to 1.1 μm is in particular at least 40% or 60%. In other words, especially red light, preferably as well as near-infrared radiation, is significantly attenuated by the color filter.

The semiconductor sensor may appear gray or black to an observer independently of the angle at least in the region of the interference filter. This means, for example, that the semiconductor sensor provides a neutral, preferably invariable optical impression independently of the angle.

The semiconductor sensor may comprise a detector chip that detects radiation of a first wavelength range, in particular green light, and an interference filter optically preceding the detector chip and permeable to radiation of the first wavelength range, in particular green light, and impermeable and reflective to radiation of a second wavelength range, in particular red light and near-infrared radiation. A color filter may optically precede the interference filter. The color filter may have a transparency of at least 60% for radiation of the first wavelength range, in particular green light, and absorbs radiation of the second wavelength range, in particular red light and near-infrared radiation. The semiconductor sensor may appear gray or black to an observer independently of the angle in the region of the interference filter.

Green-sensitive photodiodes coated with a so-called infrared cutoff filter are used, for example, in pulse measurement in fitness arm bands and fitness watches. This interference filter blocks red and near-infrared light and thus improves the signal-to-noise ratio. The blocked portion of the spectrum is reflected and results in a pink to violet appearance of the sensor. This is often undesirable for design reasons. Furthermore, interference filters exhibit a pronounced angle dependence, which leads to a comparatively bad suppression of near-infrared radiation at large incident angles.

In the semiconductor sensor, an infrared cutoff filter as an interference filter and a color filter, in particular a green filter resin which absorbs in the red, are combined with each other. The aforementioned problems can thereby be solved. A majority of the light reflected by the interference filter in the red and near-infrared spectral range is absorbed by coating the interference filter with the color filter. The semiconductor sensor thus appears dark gray to black. The color filter has an absorption minimum in the green spectral range, whereby the desired properties of the semiconductor sensor for pulse measurement are not impaired or not significantly impaired.

In this example, due to the efficient infrared suppression by the interference filter, a very thin material layer, in particular a resin layer, is sufficient for the color filter to achieve the desired color result. The residual absorption in the green spectral range by the color filter can thereby be reduced to a minimum. Furthermore, the filtering effect of the color filter is angle-independent, whereas the interference filter shifts to shorter wavelengths at larger incident angles. By combining both filters, an improved angle fidelity of the filter characteristic can be achieved overall.

The color filter may be designed as a thin layer, preferably with a consistent and constant layer thickness. An average thickness of the color filter is preferably at least 0.1 μm or 0.3 μm and/or at most 10 μm or 5 μm or 2 μm.

The color filter may be based on at least one plastic, in particular on at least one resin such as an epoxy resin. The plastic may also be a silicone, a urethane, a polymethyl methacrylate or a polycarbonate, as well as mixtures thereof. At least one filter material, in particular a dye, is preferably added to the plastic. This dye or filter material can be present in a homogeneously distributed manner in the color filter and in the plastic such that there are no intended concentration gradients. Alternatively, it is possible for color pigments to be inhomogeneously distributed, for example, sedimented in the color filter.

The color filter may be located directly on the interference filter. That is to say, the color filter and the interference filter can touch one another, in particular touch one another over the entire area.

The semiconductor sensor may comprise a cast body. The cast body is produced, for example, by casting, transfer molding or injection molding or a printing process such as screen printing. The interference filter and the detector chip may be embedded in the cast body. For example, the cast body continuously and circumferentially touches side surfaces of the interference filter and of the detector chip such that the interference filter and the detector chip can be completely framed by the cast body when viewed in plan view.

The cast body may be made of one or more plastics. At least one filter material and/or dye is at least in places added to, in particular homogeneously distributed in, the cast body. Alternatively, concentration gradients may be present, for example, due to sedimentation effects.

The cast body may extend with a thickness of at least 50 μm or 0.1 mm or 0.2 mm across the interference filter. Alternatively or additionally, the thickness of the cast body over the interference filter is at most 5 mm or 2 mm or 1 mm or 0.5 mm. In other words, the cast body is applied as a comparatively thick layer over the interference filter. In this example, the cast body over the interference filter can be thicker than the detector chip and the interference filter taken together.

The color filter may be formed by the part of the cast body extending across the interference filter. In other words, the color filter may be formed simultaneously with the formation of the cast body.

The color filter may comprise one or more of the following materials or groups of materials, or a dye or filter material of the color filter consists of one or preferably more of the following materials or groups of materials: a cyanine, an azo dye such as an azobenzene, organometallic complexes, organometallic colloids, copper II compounds such as copper (II) chloride, and quantum dots.

The color filter may be a notch filter. In this example, one or more of the aforementioned materials or groups of materials can be added to a plastic such as a filter resin. Such a filter resin is realized in particular by addition of dye molecules having a HOMO LUMO gap in the near-infrared spectral range to an otherwise transparent resin, in particular epoxy resin. As a result, a high transmission without impairment in the green spectral range and a high defined absorption in the red and/or near-infrared spectral range can be realized.

The color filter may be thinner than the interference filter. Alternatively, the interference filter may be thinner than the color filter.

The interference filter may be a high-pass filter. This means that the interference filter is permeable to high frequencies. A cutoff wavelength is preferably at least 630 nm or 645 nm and/or at most 680 nm or 670 nm, particularly in the case of perpendicular incidence of light. The cutoff wavelength is in particular the wavelength that is at half the height of a transmittance step. Thereby, a step width of the step at the cutoff wavelength is preferably at least 1 nm or 5 nm or 10 nm and/or at most 40 nm or 30 nm or 20 nm. The step width in particular indicates the wavelength range within which the transmittance increases 10% to 90% in the step.

The color filter alone, i.e., without the interference filter, may have a continuous or sporadic transmittance of at least 20% in the wavelength range between 0.6 μm and 1.1 μm. In other words, the color filter alone may be comparatively impermeable in the red and near-infrared spectral range.

The interference filter may appear reddish to an observer. This applies in particular when viewed in reflection. In other words, the interference filter alone may be a type of a reddish shimmering mirror.

The color filter alone may appear green to an observer. This applies in particular when viewed in transmission or in reflection if the color filter is located on a reflective substrate such as a white surface. If a material of the color filter is applied in a greater thickness such that a substantially opaque body results, the material of the color filter can appear brownish in reflection to an observer.

The detector chip may be a silicon detector. Then, the detector chip is photosensitive, without the use of filters, to wavelengths with energies above the bandgap of silicon, which is at a wavelength of approximately 1.1 μm.

The detector chip may be of one-channel design. Alternatively, the detector chip may be multi-channel, for example, as a result of pixelation.

A detection surface of the detector chip may have a size of at least 0.5×0.5 mm$^2$ or 1×1 mm$^2$. Alternatively or additionally, the detection surface is at most 8×8 mm$^2$ or 5×5 mm$^2$. In particular, the detection surface is approximately 3×3 mm$^2$.

The interference filter may comprise a plurality of alternating layers of a high and low refractive index. For example, at least three or five or seven such pairs of layers are present. Alternatively or additionally, the number of pairs of layers is at most 25 or 15.

The interference filter alone may have an angle-dependent, colored reflection. The angle dependence results in particular from the fact that an effective layer thickness of the layers of the interference filter increases as the incident angle increases.

The interference filter may comprise a first layer stack and a second layer stack. The two layer stacks may be configured for reflection of radiation of different wavelengths. For example, the first layer stack has a design wavelength for a reflection of at least 0.6 μm or 0.7 μm and/or at most 1 μm or 0.9 μm or 0.85 μm. Alternatively or additionally, the design wavelength for a reflection of the second layer stack is at least 0.8 μm or 0.9 μm or 0.95 μm and/or at most 1.1 μm or 1 μm or 0.9 μm. The design wavelength can be the wavelengths of maximum reflection or the wavelength that bisects a reflection window of the respective layer stack.

The color filter may be limited to the interference filter when viewed in plan view. The color filter preferably completely covers the interference filter in this example. Alternatively, it is possible for the color filter to laterally project beyond the interference filter. In the same way, the interference filter is preferably limited to the detector chip and covers it completely.

The interference filter may comprise one or more refractive index matching layers. The at least one refractive index matching layer reduces a refractive index jump at the interference filter in a direction away from the detector chip. It is possible that the refractive index matching layer delimits the interference filter toward the color filter and is directly attached to the color filter such that the color filter can touch the refractive index matching layer.

The interference filter may be located directly on the detector chip. For example, the interference filter is produced by a vapor deposition method, in particular PVD or CVD directly on a main side of the detector chip, preferably when it is still in the wafer composite.

The semiconductor sensor may be configured for pulse measurement. That is to say, the semiconductor sensor, for example, may be applied directly to human skin. A read-out frequency of the semiconductor sensor is high enough to allow pulse measurement.

Hereinafter, a semiconductor sensor described herein is explained in more detail with reference to the drawing based on examples. In this respect, identical reference symbols indicate identical elements in the individual figures. However, no true-to-scale relationships are shown. Rather, individual elements may be shown in an exaggeratedly large manner for better understanding.

FIG. 1 illustrates an examples of a semiconductor sensor 1. The semiconductor sensor 1 comprises a detector chip 2, an interference filter 3 and a color filter 4. The two filters 3, 4 are arranged congruently above the detector chip 2.

A detection side 10 of the semiconductor sensor 1 through which radiation passes to the detector chip 2 is formed by the color filter 4. A mounting side 11 to which the semiconductor sensor 1 is mounted is formed by the detector chip 2.

Figure 2:
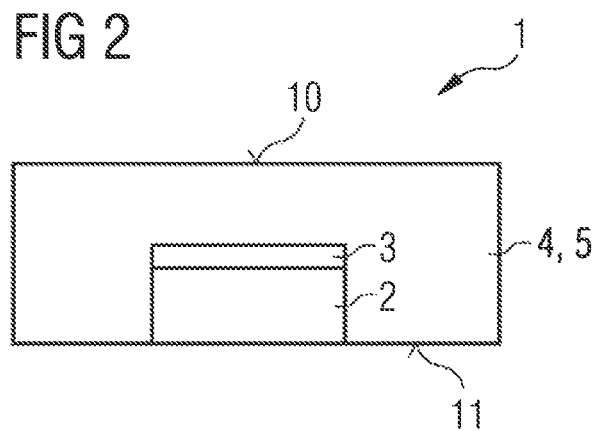

In the example of FIG. 2, the color filter 4 is realized by a cast body 5 extending with a comparatively large thickness across the interference filter 3. The interference filter 3 and the detector chip 3 are embedded in the cast body 5. The mounting side 11 is formed by the detector chip 2 together with the cast body 5. In a plan view (not shown), the cast body 5 preferably circumferentially surrounds the detector chip 2 in a closed path, in particular with a constant thickness.

Figure 3:
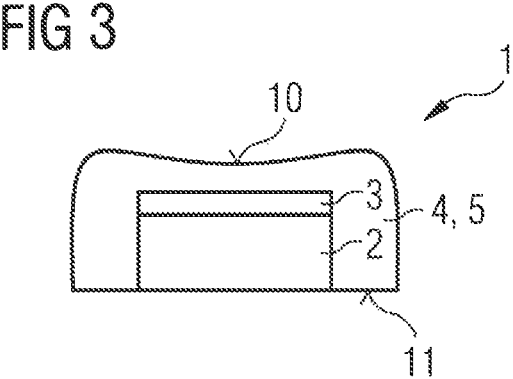

FIG. 3 illustrates that the color filter 4 is formed by a layer having a slightly varying layer thickness both on the detection side 10 and on side surfaces. Such a cast body 5 for the color filter 4 can be produced, for example, by a printing method.

Due to the manufacturing method, for example, the color filter 4 has a thickness profile on the detection side 10. The color filter 4 can be made to be thicker over side edges of the detector chip 2 than in a central region. In other words, the color filter 4 has a concave profile on the detection side 10. Since the color filter 4 serves substantially to adjust the optical appearance of the semiconductor sensor 1 and only secondarily to suppress radiation not to be detected, such thickness profile of the color filter 4 can be tolerated without a loss of function.

Figure 4:
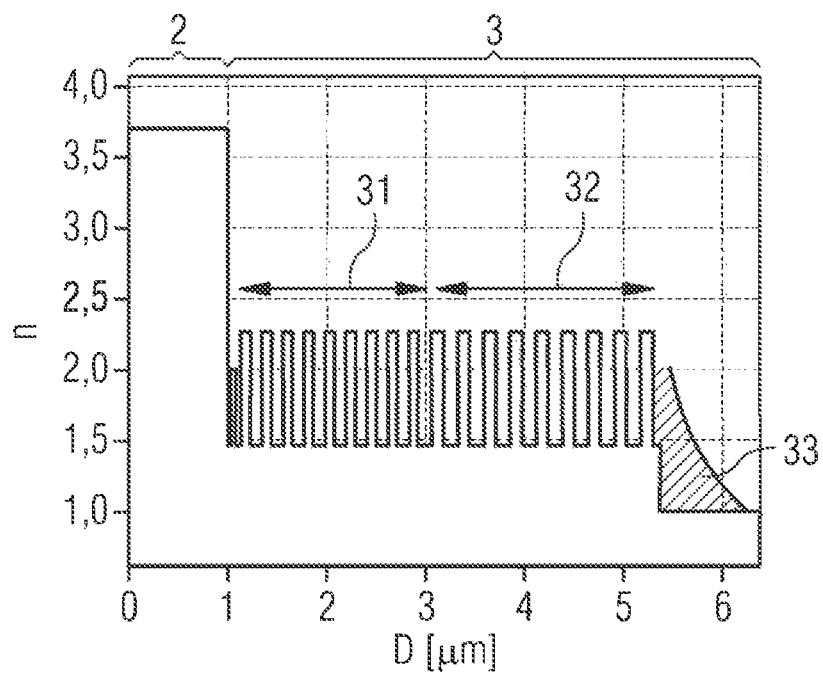
FIG. 4 is a schematic sectional view of an interference filter for semiconductor sensors described herein.

FIG. 4 schematically illustrates a preferred interference filter 3 for the semiconductor sensor 1. A refractive index n, in particular for green light, is plotted over a position D along a growth direction.

The interference filter 3 is mounted directly on the detector chip 2 and comprises a first layer stack 31 and a second layer stack 32. The two layer stacks 31, 32 are configured for reflection of different wavelengths or wavelength ranges. For example, a design wavelength of the first layer stack 31 is approximately 780 nm and a design wavelength of the second layer stack 32 is approximately 980 nm. Reflection ranges of the two layer stacks 31, 32 each have widths of approximately 300 nm and are designed such that they overlap one another and extend across a band edge of the silicon-based detector chip 2, i.e., for example, up to a wavelength of at least 1.2 µm or 1.3 µm.

Optionally, a refractive index matching layer 33 is present, indicated with shading in FIG. 4. A gradual refractive index transition in the direction away from the detector chip 2, for example, toward the color filter 4, is achieved by the refractive index matching layer 33.

Figure 5:
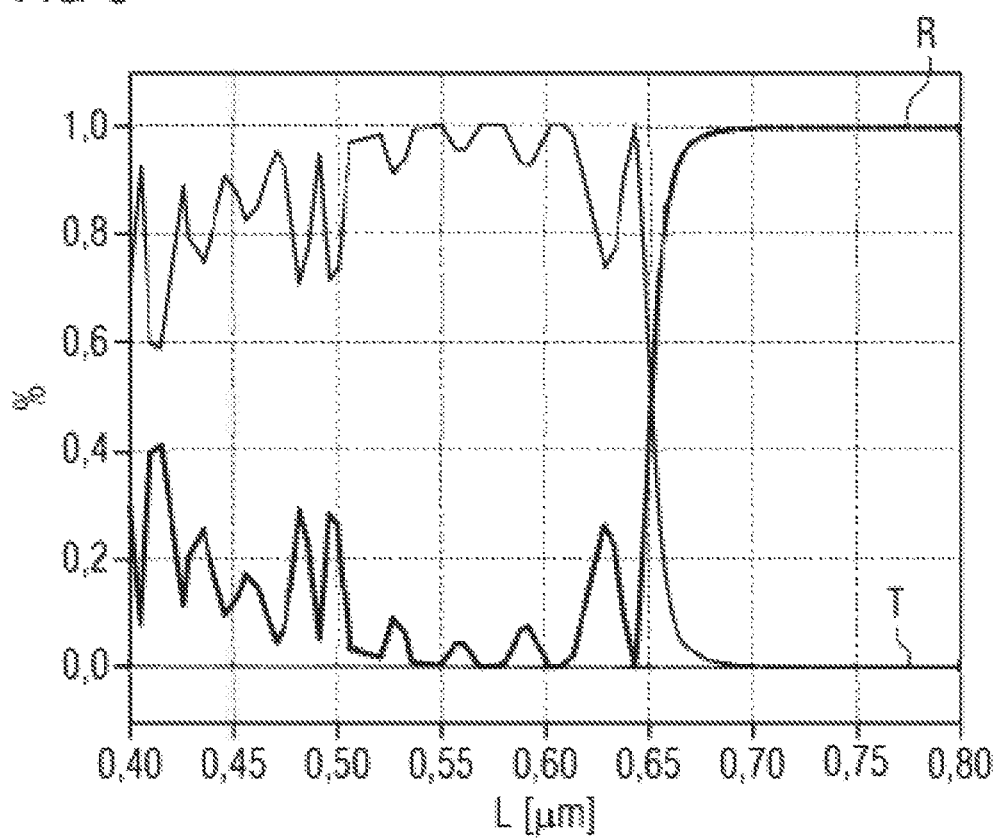
FIGS. 5 to 9 are schematic illustrations of optical properties of semiconductor sensors described herein.

In FIG. 5, a reflectivity R and a transmission T of the interference filter 3 of FIG. 4 are plotted over the wavelength L, in percent. A cutoff wavelength at the intersection of the curves for the transmission T and the reflectivity R is approximately 660 nm. Above approximately 670 nm, the interference filter 3 is virtually impermeable.

Figure 6:
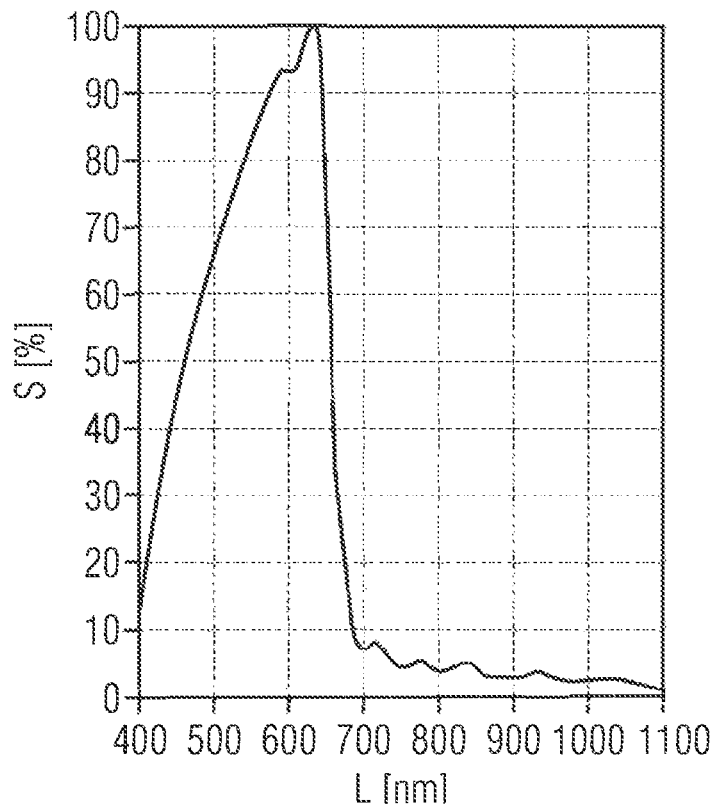

In FIG. 6, the relative spectral sensitivity S only with the interference filter 3 is plotted over the wavelength L. The sensitivity S of the detector chip 2 is thus substantially limited by the interference filter 3 to the blue, green and red spectral range. Near-infrared radiation is almost completely suppressed.

A smoothing of the reflectivity R and the transmission T, as can be seen in FIG. 5, can be achieved, for example, by the refractive index matching layer 33 as illustrated in FIG. 4.

Figure 7:
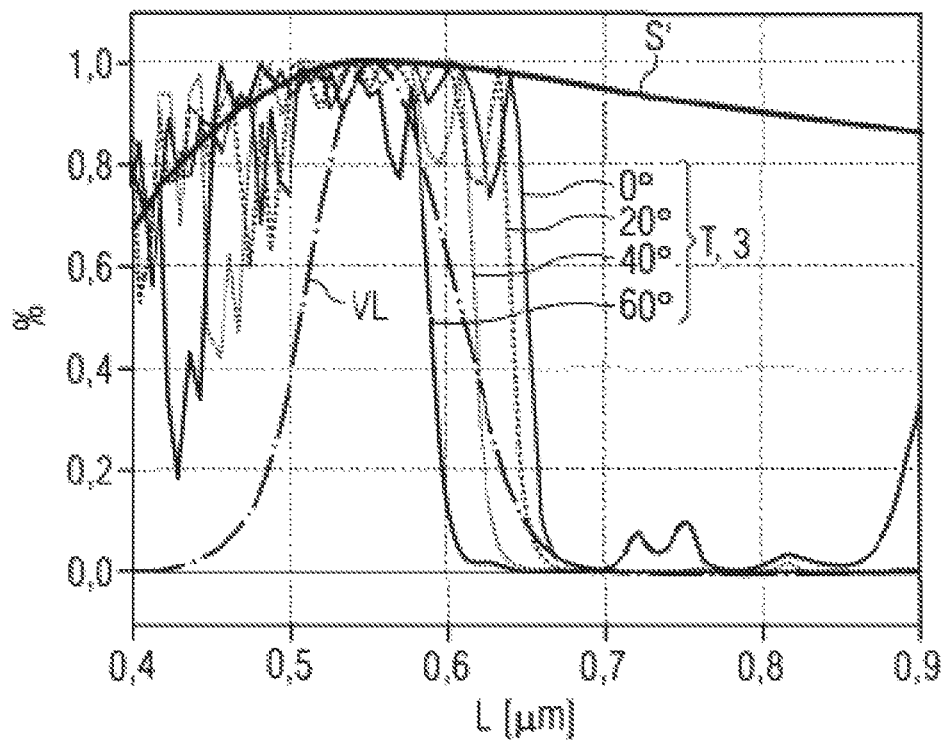

FIG. 7 shows the transmission T of the interference filter 3, in particular of FIG. 4, for different incident angles. The eye sensitivity curve VL is also plotted.

With an increasing incident angle, the cutoff wavelength shifts to the short-wave spectral range. As a result, an overlap of the transmission T and thus of the reflectivity (cf. FIG. 5) changes with the eye sensitivity curve VL. Thus, at an incident angle of 0°, the interference filter 3 still appears dark gray or black, but with increasing angle and associated greater overlap with the eye sensitivity curve VL, the interference filter 3 increasingly provides a disturbing red color impression to an observer.

Figure 8:
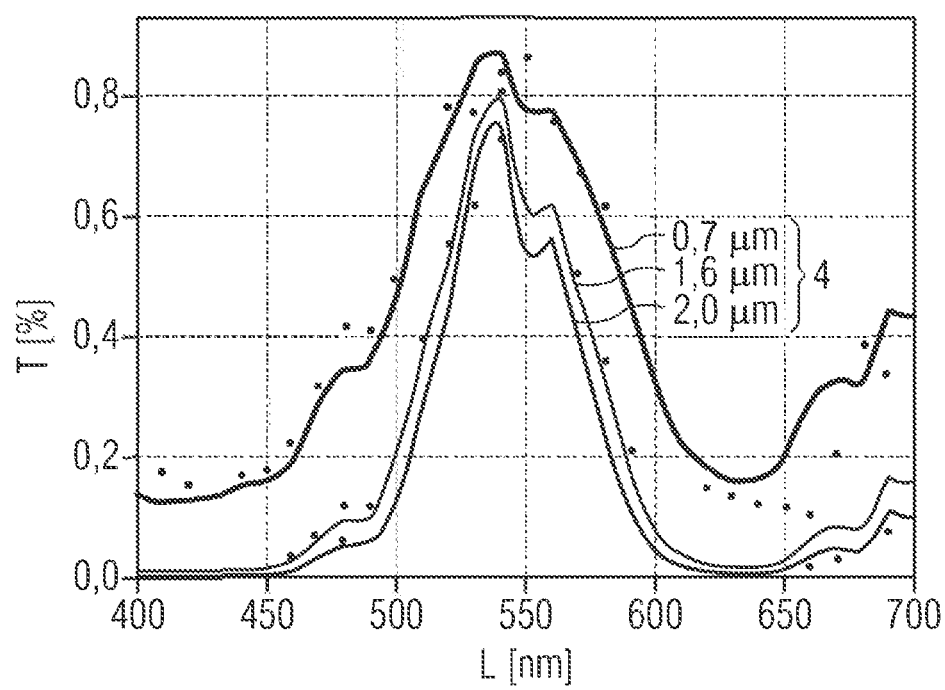

In FIG. 8, the transmission T of the color filter 4 alone is plotted over the wavelength L for various material thicknesses. Even with comparatively small thicknesses of 1.6 µm or 2 µm, the transmittance T in the green spectral range decreases significantly by 540 nm. The color filter 4 is thus preferably to be applied in only a thin layer.

Figure 9:
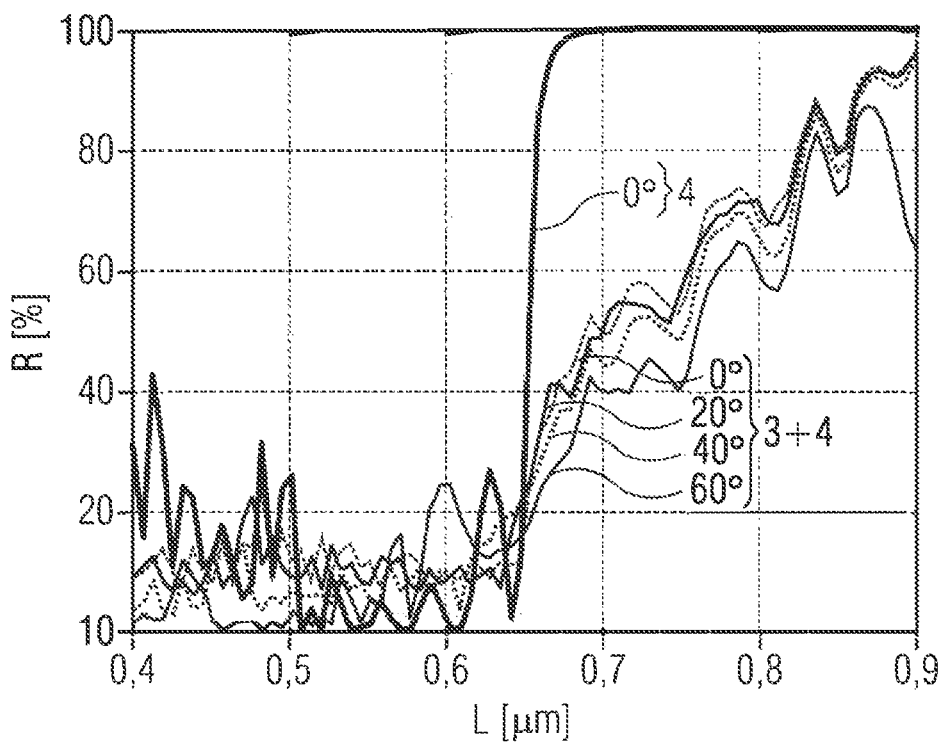

In FIG. 9, the resulting transmission T for various angles is indicated with respect to the wavelength L when the interference filter 3 of FIG. 4 is combined with the color filter 4 of FIG. 8. The transmission T of the color filter 4 alone is also plotted. In this example, the color filter 4 has a thickness of only 0.5 µm.

It can be seen in FIG. 9 that reflectivity of the interference filter 3 in the red and near-infrared spectral range is strongly suppressed by the color filter 4, specifically the more the greater the incident angle is. This results in an almost constant, in particular colorless, appearance of the filter combination of the interference filter 3 together with the color filter 4 independently of the angle.

Examples of manufacturing methods for the semiconductor sensor 1 are schematically illustrated in FIGS. 10 to 12. According to FIG. 10, production takes place in the wafer composite. In the process, a wafer with the detector chips 2 is preferably mounted on a temporary carrier 6. The interference filter 3 is produced as a coherent layer. The color filter 4 is applied directly to the interference filter 3 as a thin, uniform layer, for example, by spin coating.

The semiconductor sensors 1 are separated along separation lines 7. Before or even after separation, the semiconductor sensors 1 are preferably detached from the carrier 6. It is possible that the carrier 6 is not affected or only slightly affected by the separation.

According to FIG. 11, the color filter 4 is produced as a cast body 5. In this example, the detector chips 2 provided with the interference filter 3 are preferably mounted on the carrier 6. The carrier 6 can be an expandable film applied to the detector chips 3 not yet separated in the wafer composite. After sawing the wafer of the detector chips 2, the carrier 6 can then be stretched such that a gap is formed between adjacent detector chips 2, which gap is provided with the material for the cast body 5. Between the detector chips 2, separation takes place along the separation lines 7.

FIG. 12 shows that the color filter 4 is applied locally to the individual detector chips 2 with the interference filters 3, for example, by a printing method or a mask process.

A material of the color filter 4 may extend concavely across the detection side 10. It is possible that the material of the color filter 4 partly or, in deviation from the representation in FIG. 12, also completely covers side surfaces of the interference filters 3 and of the associated detector chips 2. Alternatively, it is possible, in deviation from the representation in FIG. 12, that the material of the color filter 4 is limited to a top side of the interference filter 3 facing away from the temporary carrier 6.

Unless otherwise indicated, the components shown in the figures preferably directly follow one another in the order indicated. Layers that do not touch in the figures are spaced apart from one another. Insofar as lines are drawn in parallel to one another, the respective surfaces are likewise aligned in parallel to one another. Unless otherwise indicated, the relative positions of the drawn components relative to one another are also correctly reproduced in the figures.

Our sensors and methods as described herein are not limited by the description based on the examples. Rather, this disclosure encompasses any novel feature as well as any combination of features, including in particular any combination of features in the appended claims, even if such feature or combination itself is not explicitly specified in the claims or examples.

This application claims priority of DE 10 2017 113 535.9, the subject matter of which is incorporated herein by reference.

The invention claimed is:

1. A semiconductor sensor comprising:
   a detector chip that detects radiation of a first wavelength range or green light,
   an interference filter that optically precedes the detector chip and is permeable to the radiation of the first wavelength range or the green light, and impermeable and reflective to radiation of a second wavelength range or red or near-infrared light,
   a color filter that optically precedes the interference filter, wherein
   the color filter has a transparency of at least 60% for the first wavelength range or green light, and absorbs radiation of the second wavelength range or red or near-infrared light, and
   the semiconductor sensor appears gray or black to an observer in a region of the interference filter independently of the angle,
   the interference filter comprises at least one refractive index matching layer that delimits the interference filter toward the color filter, and
   a cast body in which the interference filter and the detector chip are embedded, wherein the cast body contains least one plastic to which at least one filter material is added, and the cast body extends across the interference filter so that the color filter is formed by the part of the cast body extending across the interference filter.

2. The semiconductor sensor according to claim 1,
wherein the color filter has an average thickness of 0.1 μm to 5 μm and is based on at least one plastic, and the first wavelength range is the green light and the second wavelength range is the red or near-infrared light.

3. The semiconductor sensor according to claim 1, wherein the cast body extends with a thickness of 0.1 mm to 1 mm across the interference filter.

4. The semiconductor sensor according to claim 1, wherein the color filter comprises one or more of: a cyanine, an azo dye, organometallic complexes, organometallic colloids, and a copper II compound.

5. The semiconductor sensor according to claim 1, wherein the color filter comprises or consists of a metal dielectric filter, and the color filter is thinner than the interference filter.

6. The semiconductor sensor according to claim 1,
wherein the interference filter is a high-pass filter that exhibits a cutoff wavelength of 630 nm to 680 nm in a perpendicular incidence of light, and a step width of the transmittance at the cutoff wavelength is 10 nm to 40 nm.

7. The semiconductor sensor according to claim 1, wherein the color filter alone continuously exhibits a transmittance of at least 20% in the wavelength of 600 nm to 1.1 μm.

8. The semiconductor sensor according to claim 1, wherein the interference filter alone appears reddish to an observer and the color filter alone appears green.

9. The semiconductor sensor according to claim 1,
wherein the detector chip is a one-channel design and based on silicon, and a detection surface of the detector chip is 0.5×0.5 mm$^2$ to 5×5 mm$^2$.

10. The semiconductor sensor according to claim 1,
wherein the interference filter comprises a plurality of alternating layers having a high and low refractive index, and the interference filter alone exhibits an angle-dependent colored reflection.

11. The semiconductor sensor according to claim 1,
wherein the interference filter comprises a first layer stack and a second layer stack, the first layer stack exhibits a design wavelength for a reflection of 0.6 μm to 0.9 μm, and the second layer stack exhibits a design wavelength for a reflection of 0.8 μm to 1.1 μm.

12. The semiconductor sensor according to claim 1, wherein the color filter is limited to the interference filter when viewed in plan view.

13. The semiconductor sensor according to claim 1, wherein a gradual refractive index transition in a direction away from the detector chip toward the color filter is achieved by the refractive index matching layer.

14. The semiconductor sensor according to claim 1, wherein the interference filter is applied directly to the detector chip.

15. The semiconductor sensor according to claim 1, wherein said semiconductor sensor is configured for pulse measurement.

* * * * *